United States Patent [19]
Vandenberg

[11] Patent Number: 5,921,970
[45] Date of Patent: *Jul. 13, 1999

[54] LARGE VARIABLE DIAMETER MEDICAL SUCTION SYSTEM

[76] Inventor: James T. Vandenberg, 17847 Bald Hills Rd., Yelm, Wash. 98597

[ * ] Notice: This patent is subject to a terminal disclaimer.

[21] Appl. No.: 08/912,723

[22] Filed: Aug. 18, 1997

Related U.S. Application Data

[63] Continuation-in-part of application No. 08/613,251, Mar. 8, 1996, Pat. No. 5,665,080.
[51] Int. Cl.$^6$ .................................................. A61M 1/00
[52] U.S. Cl. ............................................. 604/264; 604/275
[58] Field of Search ...................................... 604/317, 318, 604/319, 119, 163, 94, 96, 905, 283, 275, 276, 264; 128/202.14, 202.15, 202.27, 202.28; 15/309.1

[56] References Cited

U.S. PATENT DOCUMENTS

| | | |
|---|---|---|
| 4,221,220 | 9/1980 | Hansen . |
| 4,273,126 | 6/1981 | Grane et al. . |
| 4,319,570 | 3/1982 | Grane . |
| 4,455,140 | 6/1984 | Joslin . |
| 4,490,138 | 12/1984 | Lipsky et al. . |
| 4,662,367 | 5/1987 | Gore, Jr. . |
| 4,925,447 | 5/1990 | Rosenblatt . |
| 5,002,534 | 3/1991 | Rosenblatt . |
| 5,109,565 | 5/1992 | Akin et al. ................................ 15/309 |
| 5,114,415 | 5/1992 | Shedlock . |
| 5,251,619 | 10/1993 | Lee . |
| 5,419,769 | 5/1995 | Devlin et al. . |
| 5,665,080 | 9/1997 | Vandenberg ............................. 604/319 |

*Primary Examiner*—John G. Weiss
*Assistant Examiner*—David Cho
*Attorney, Agent, or Firm*—Richard C. Litman

[57] ABSTRACT

A large diameter medical suctioning system for rapid evacuation of fluid foreign matter from patients using an increased diameter suction tube and a variable diameter suction tip. The variable diameter suction tip is expandable to a diameter of between ⅜ of an inch and 2 inches. The suction tube and connections thereto have a correspondingly increased diameter that provides an evacuation rate at least 10 times faster than the rate of evacuation using conventional suction systems. Additionally, the variable diameter suction tip is capable of performing the functions of a conventional suction tip by reducing the diameter of the variable diameter suction tip. The large diameter suctioning system is configured for connection to the pour spout of a suction canister to assure compatibility with existing medical vacuum systems.

11 Claims, 4 Drawing Sheets

LARGE VARIABLE DIAMETER MEDICAL SUCTION SYSTEM

CROSS REFERENCE TO RELATED APPLICATION

This is continuation-in-part of Ser. No. 08/613,251, filed Mar. 8, 1996, U. S. Pat. No. 5,665,080.

BACKGROUND OF THE INVENTION

1. Field of the Invention

The present invention relates to an improved suctioning device for rapid evacuation of fluid foreign material. The invention is particularly useful as an oropharyngeal suctioning device capable of rapidly removing chunky vomitus and bodily secretions and as a surgical suctioning device during exploratory laparotomy for rapidly clearing the surgical field to enable identification of ruptured blood vessels.

2. Description of Related Art

In emergency and surgical care hospital and medical provider settings, aspiration of regurgitated gastric contents in patients with an altered gag reflex (e.g., unconscious or anesthetized) is a life-threatening event. Mortality rates as high as seventy percent have been associated with massive aspiration of gastric contents. It is known that as little as twenty milliliters of gastric contents (approximately ⅕ mouthful) can cause significant lung damage when aspirated.

Treatment is simple: evacuation of the airway of the patient prevents the foreign matter from passing from the oropharyngeal cavity into upper airway passages and beyond. However, two factors affect the success of treatment. First, the time needed to evacuate the oropharyngeal cavity and airway of a patient is obviously of the essence; if vomitus can be expeditiously removed, patient morbidity and mortality should be positively influenced. Second, complete removal of vomitus and secretions is also important to prevent aspiration of secretions and minute particles after the bulk of the vomitus has been removed. Moreover, the medical care provider must maintain a sensitivity to possible soft-tissue damage within the oropharyngeal cavity caused by the suction tip during overzealous suctioning. Thus, a balance must be maintained between the need for speedily clearing a large volume of variably sized vomitus and the need for precise removal of residual secretions.

Under ideal medical care provider circumstances, removal of the regurgitated materials begins immediately after emesis. A commonly employed suction system comprises a thick-walled vacuum tubing (usually ¼ inch inside diameter, 8 to 10 feet in length) with a suction tip for collection of vomitus from the oropharynx of a patient. The tubing is connected to a collection canister attached to a wall-mounted vacuum inlet or regulator, which is in turn connected to a central vacuum line. Standard hospital regulations require that central vacuum line systems must be capable of generating at least 304 mm Hg at any inlet, the norm ranging between 381 mm Hg and 482 mm Hg.

However, surprisingly, such standard and commonly used hospital suction equipment is inadequate for removing both chunky vomitus and the remaining secretions. Medical literature reveals that a standard hospital setup having a vacuum pressure of 550 mm Hg required 7.5 seconds to evacuate 140 milliliters of simulated vomitus, a period of time concluded to be too long to prevent clinically significant aspiration.

Moreover, commonly used suctioning tips, such as Yankauer tips also having a ¼ inch inside diameter or less, are designed primarily for applications wherein a capability to evacuate every drop of essentially solid-free liquids or secretions (at most contaminated by small solid chips such as might be encountered during surgery) from a surface is desired. However, such tips become easily and entirely blocked by chunky vomitus. Clearing the blockage in an emergency situation requires additional precious time. Thus, reliable and effective suction equipment capable of clearing the oropharynx of secretions and chunky vomitus in a timely manner is a critical component of an emergency resuscitation procedure.

The present invention reduces the evacuation time by improving suction efficiency of such hospital suction setups. Increasing the diameter of suction tips, tubing, and connectors leading to the suction port of a suction canister increases the rate of flow through the suction device. No studies of the medical literature were found addressing suction device internal diameters to improve suction efficiency.

The prior art likewise discloses no suction apparatus or combination of components thereof having an inlet capable of being expeditiously increased to a critical range of diameters suitable for the rapid evacuation of fluid foreign material including chunky vomitus and bodily secretions. U.S. Pat. No. 4,490,138, issued Dec. 25, 1984, to Lipsky et al., discloses a pharyngeal suction device including a hollow wand and a safety tip attached thereto. U.S. Pat. No. 4,273,126 issued Jun. 16, 1981 to Grane et al. describes a hand-held attachment device for use with a tracheal aspirator directed at collection of large, solid particles from the trachea and mouth of a patient. U.S. Pat. No. 4,221,220, issued Sep. 9, 1980, to Hansen, discloses a surgical suction nozzle for removing vomitus from unconscious patients that is resistant to clogging.

Other patents reveal a wide range of applications for suction collection devices, none of which describe a combination of similar structural components directed at improving the rate of fluid flow of secretions containing solid particles to a collection container. For example, U.S. Pat. No. 4,455,140 issued Jun. 19, 1984 to Joslin describes a collapsible fluid collection device having telescopically disposed members directed at reducing its storage space. U.S. Pat. No. 4,319,570 issued Mar. 16, 1982 to Grane describes a tracheal suction pump driven by compressed gas and designed primarily for aspiration of vomitus and secretions. U.S. Pat. No. 4,925,447 issued May 15, 1990 to Rosenblatt describes an aspirator containing a bellows to isolate gases and liquids collected from the patient from the source of the suction. U.S. Pat. No. 5,002,534, issued Mar. 26, 1991, to Rosenblatt shows a potable, manually operated aspirator including a container. U.S. Pat. No. 5,251,619, issued Oct. 12, 1993, to Lee, discloses a tracheal tube including a sealant cuff. U.S. Pat. No. 5,419,769 issued May 30, 1995 to Devlin et al. describes a suction system employing a suction control device which allows manual control of application of reduced pressure in the system. U.S. Pat. No. 4,662,367 issued May 5, 1987 to Gore, Jr. describes a trachea suction tube for removing an obstruction by placing one end over laryngeal surfaces of a patient and by orally drawing air through the tube from the other end. U.S. Pat. No. 5,114,415 issued May 19, 1992 to Shedlock describes a soft, flexible adapter shallowly inserted into the nostril for suctioning secretions from upper airways.

None of the above inventions and patents, taken either singly or in combination, is seen to describe the instant invention as claimed.

SUMMARY OF THE INVENTION

The present invention relates to an improved suctioning device for rapid evacuation of fluid foreign matter, defined herein as including vomitus and bodily secretions. The improved suctioning device for evacuation of fluid foreign matter from patients uses a ¾ inch inside diameter tubing and similarly increased diameter suction tip. This increase in diameter provides an evacuation rate of at least 10 times faster than the rate of evacuation using the prior art devices. The improved suctioning device includes a suction tip having an increased diameter ranging between ⅜ of inch and 2 inches, a patient vacuum tubing of an inside diameter between ⅜ of an inch and 2 inches and 4 to 10 feet in length, a first adapter for attaching the tubing to a pour spout of a suction canister with inside diameter measuring at least ½ of an inch and a second adapter for connecting the suction tip to the tubing. A central vacuum line inlet is provided to apply negative pressure to the canister.

Accordingly, it is a principal object of the invention to provide an suctioning device for the rapid evacuation of fluid foreign matter including vomitus and bodily secretions from the oropharyngeal cavity to positively affect the morbidity and mortality of patients subject to a risk of aspiration of fluid foreign matter.

It is a further object of the invention to provide a suctioning device for the rapid clearing of the surgical field during procedures such as exploratory laparotomies during which rapid identification of ruptured blood vessels is required to prevent morbidity and mortality of patients.

It is another object of the invention to provide a suctioning device with an adjustable inlet diameter to immediately provide an increased internal diameter suction system permitting the rapid emergency evacuation of substantial quantities of fluid foreign matter including solids.

It is a further object of the invention to provide a suctioning device having components adapted for use with components of suctioning devices found in the prior art.

Still another object of the invention is to provide an oropharyngeal suctioning device having components which permit an evacuation procedure to be conducted in a standard medical care facility setting.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

The present invention relates to an improved suctioning device for rapid evacuation of fluid foreign material including chunky vomitus and bodily secretions wherein a range of internal diameters of the components of a suction system connected to a central vacuum line improves suction efficiency for the intended purpose.

As matter of background, the rate of flow through a uniform tube as defined by Poiseuille's Law is controlled by the following variables: the pressure difference applied, the length of the tube, the viscosity coefficient of the fluid, and the radius of the tube. Poiseuille's Law is stated as follows:

$$R=(p_1-p_2)(\pi r^4)/8\eta L$$

where R is rate of flow; $p_1-p_2$ is the pressure difference applied; r is the radius of the tube; $\eta$ is the viscosity coefficient; and, L is the length of the tube.

Figure 4:
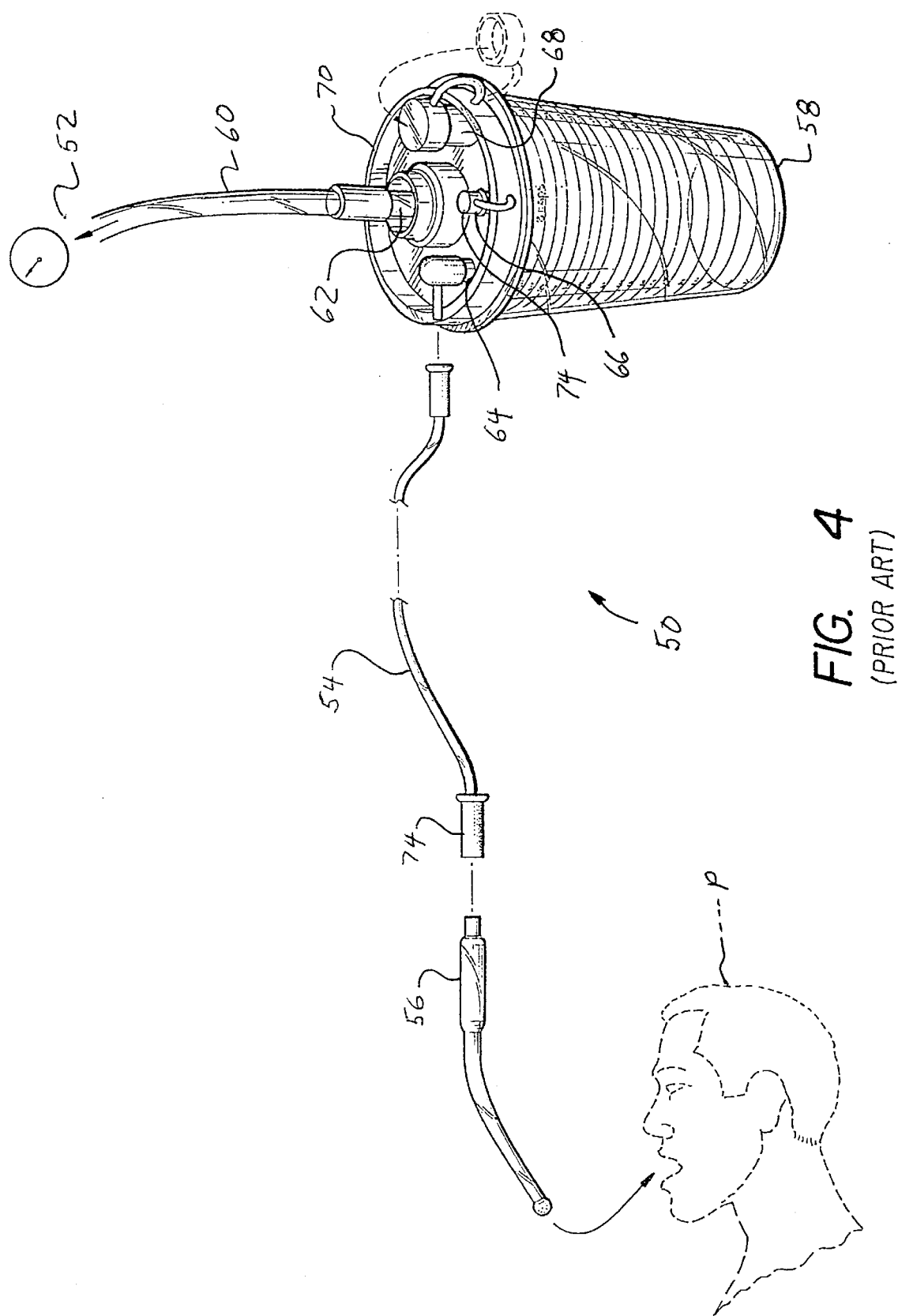
FIG. 4 is an environmental, perspective, exploded view of a suction device known in the prior art showing its components and connections.

In the present application of Poiseuille's Law, all variables but the radius of the tube are limited by external factors. Referring first to FIG. 4, the limiting factors can be explained relative to a commonly used suctioning system 50 as found in the prior art.

First, the pressure difference variable is dependent upon the negative pressure source normally supplied at the wall inlet of a central vacuum line of a hospital or medical care provider facility (as represented by the regulator dial 52), which negative pressure as previously noted ranges between 381 mm Hg and 482 mm Hg. Moreover, an optimal suction pressure has been described in medical literature at which potential injury to the oropharynx of a patient is limited. Thus, at any one hospital facility, the applied pressure difference at a central vacuum line inlet 52 is constant for purposes of maximizing suction efficiency from a central vacuum line inlet 52.

Next, the length of a patient suction tube 54 must be capable of reaching from the wall inlet 52 to a patient P, limited therefore to no less than 4 feet in length, and has traditionally been found to provide acceptable range at 8 feet in length. Although clearly the length of tubing can be shortened to increase rate of flow, standard practice and experience in hospital settings dictate that 8 feet is a necessary length of tubing associated with emergency facility settings and equipment available for evacuation of vomitus.

The viscosity coefficient for vomitus is also effectively a constant and, for experimentation purposes, has been simulated by vegetable soup. The vomitus must travel from the mouth of the patient P over the length of the tubing 54 plus the length of a suction tip 56 (employed to safely suction the oropharynx of the patient) to a suction canister 58. Although the suction tip adds to the overall length of the tubing, the suction tip 56 is commercially produced standard in length and comparable in length to alternate or substitute suction tips used in the medical profession for similar applications. Traditionally, a standard Yankauer suction tip has been the instrument of choice for evacuation of vomitus. The standard Yankauer suction tip has a tip inside diameter of no more than ¼ inch and a length of approximately 12 inches. Standard practice and experience in hospital settings dictate that the additional constant length associated with the suction tip for evacuation of vomitus is necessary for safe and efficient procedure.

A suction canister 58 is necessary to collect evacuated vomitus and secretions and is designed to prevent aspiration of foreign material into the central vacuum line inlet 52. A vacuum inlet tube 60 is connected to a vacuum inlet port 62 of a canister lid 70 to create a negative pressure in the canister 58. A standard commercially produced canister 58 provides a ¼ inch patient tubing port 64 for connection of the patient suction tubing 54, and a smaller diameter 3/16 inch patient tubing port 66 (shown capped by a removable cap 72). All caps are removable such that ports may be interchangeably used. Suitable connectors 74 may be used as necessary to provide a sealed, continuous path to the suction canister 58. A pour spout 68 of at least a ¾ inch diameter (shown capped) is provided for removal of the evacuated materials from the canister 58.

Therefore, given the above limiting factors, the radius of the suction system is effectively the only variable by which the rate of flow can be increased to increase suction efficiency in a hospital setting providing a central vacuum line and standard suction equipment.

Figure 1:
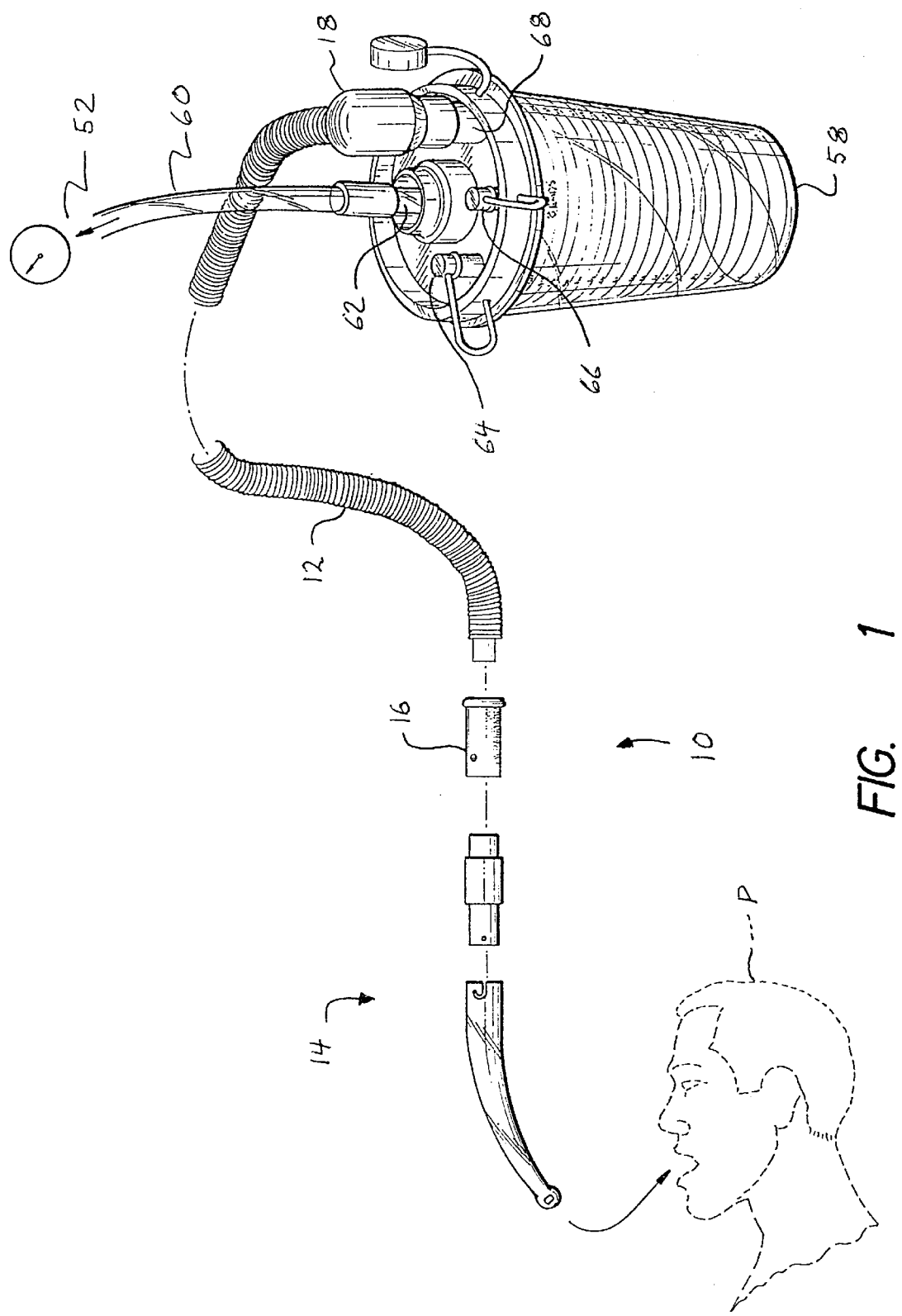
FIG. 1 is an environmental, perspective, exploded view of the suction device of the present invention showing its components and connections.

The present invention 10, as shown in FIG. 1, provides a combination of components, in part using components of the equipment as shown in FIG. 4, which are adapted such that patient suction tubing 12 having an inside diameter between ⅜ inch and 2 inches is used. The inventor has determined in experiments simulating evacuation of vomitus (maintaining the above noted constants, using a ¾ inside diameter patient suction tubing 12) that vegetable soup is evacuated at a rate at least 10 times faster than the rate of evacuation using the prior art as shown in FIG. 4.

The present invention 10 includes a suction tip 14 having tip orifice of adjustable size, a patient suction tube 12 of an inside diameter between ⅜ inch and 2 inches and 4 to 10 feet in length. Patient suction tubing may be reinforced to prevent the larger diameter tubing from kinking and thus obstructing the suction flow. Two connectors are provided. A first adapter 18 for connecting the patient suction tube 12 to the pour spout 68 of a suction canister 58. The pour spout 68 has a diameter of at least ½ of an inch. A second adapter 16 connects the suction tip 14 with the patient vacuum tubing 12. A central vacuum line inlet 52 is provided to apply negative pressure to the canister 58 by means of the vacuum inlet tube 60 attached to the vacuum inlet port 62 of the canister 58. Each of the patient ports 64, 66 are capped to provide an air-tight seal to maintain the negative pressure within the canister 58.

Figure 2:
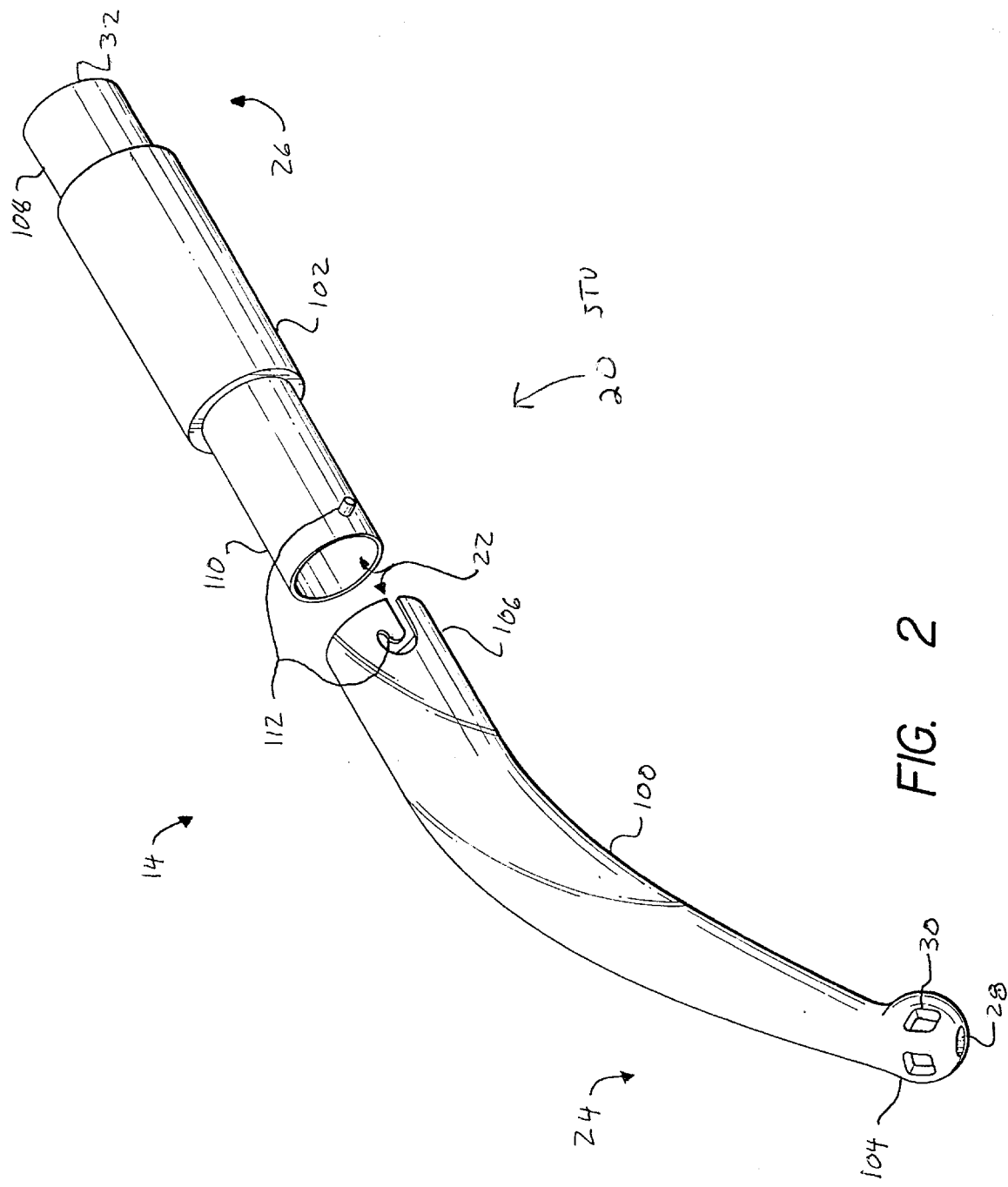
FIG. 2 is a perspective, exploded view of a suction tip of the suction device as shown in FIG. 1.

The suction tip 14 having a adjustable tip orifice is shown in FIG. 2. The suction tip 14 includes a barrel 20 that defines a lumen 22 passing longitudinally therethrough. The barrel 20 has an tip end 24 and an opposite connection end 26. The tip end 24 includes an inlet opening 28. The inlet 28 is configured as a standard Yankauer bulb tip being smoothly contoured and having relief eyes 30 to prevent damage to soft tissue during normal suction operation. Barrel 20 is bent or curved for ease of use. The suction tip 14 has all of the advantages of the prior art suction tips 56. Suction tip 14 is capable of effectively removing all the fluid in a cavity without damaging the soft tissue in the cavity. The connection end 26 of barrel 20 defines a discharge outlet 32 for connection to the patient suction tube 12. The lumen 22 connects the inlet 28 with the discharge outlet 32.

The barrel 20 is divided into two parts: a nozzle 100 at tip end 24 and a handle 102 at connection end 26. The handle 102 has a first end 108 and an opposite second end 110. The first end 108 is configured for attachment to the patient suction tube 12. The nozzle 100 has an inlet end 104, which includes inlet 28, and an opposite attachment end 106. The nozzle 100 and the lumen 22 are tapered from attachment end 106, which has a large cross sectional area, to inlet end 104, which has a relatively smaller cross sectional area. Nozzle 100 is curved or bent for ease of use. The inlet 28 has a diameter of approximately ¼ of an inch to provide the advantages of conventional suction tips. To provide the high flow rate possible from the large diameter suction system, the diameter of the lumen 22 increases to a large diameter of from ⅜ of an inch to 2 inches. The preferred diameter is ¾ of an inch as suction is frequently broken by air passage if the diameter is increased beyond ¾ of an inch.

Attachment means 112 are provided for attaching the attachment end 106 of the nozzle 100 to the second end 110 of the handle 102. Attachment means 112 provide means for positively securing the nozzle 100 to the handle 102 while permitting the nozzle 100 to be quickly removed during events requiring increased suction flow rate. Attachment means 112 that provide the necessary quick release include the twist lock pin and channel combination shown, friction joined fittings, matting screw threads, and latches.

During most surgical operations, the suction system 10 is used with nozzle 100 secured to handle 102 and functions as a conventional suction system with all the advantages of a conventional suction tip. During surgical situations where immediate removal of fluid foreign matter is critical, the nozzle 100 is quickly detached from the handle 102 to expose the large diameter of lumen 22 at the junction of the handle 102 and the nozzle 100. Upon detachment of nozzle 100 from handle 102, lumen 22 at the first end 110 forms the tip orifice. The large diameter tip orifice and large diameter patient suction tube 12 connected to the large diameter pour spout 68 of suction canister 58 provide a suction system having an increased flow rate that is not obstructed by solids in the fluid matter removed. This immediate conversion from a conventional suction system that is able to gently remove fluids to the increased diameter system able to remove chunky fluid material at a high flow rate is particularly useful when suction speed is critical such as after emesis to prevent aspiration of vomitus and during heavy internal bleeding to clear the surgical field.

Figure 3:
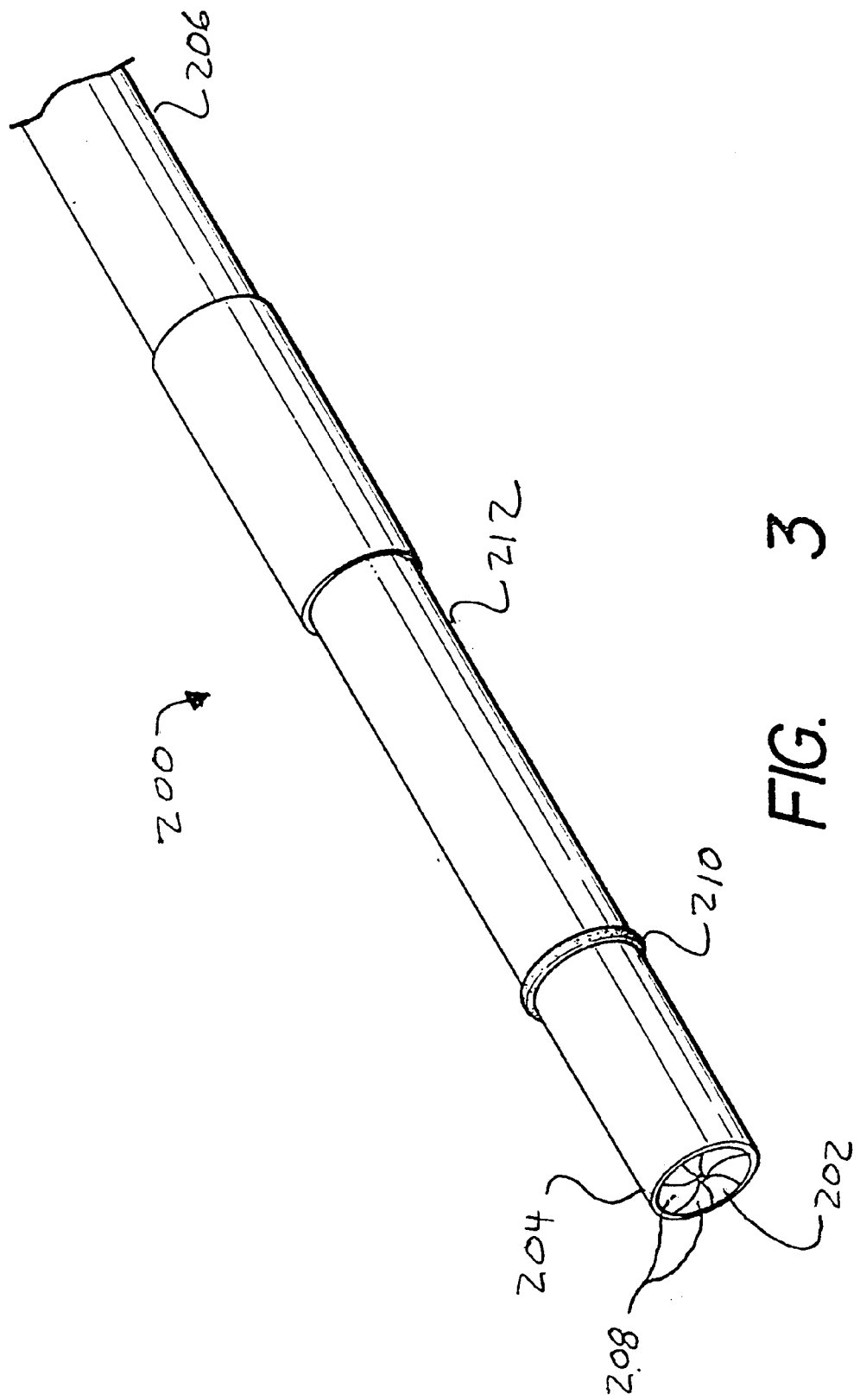
FIG. 3 is a perspective view of an alternative embodiment of the suction tip.

A second embodiment of the suction tip of the present invention is shown in FIG. 3. Suction tip 200 includes a barrel 212 having a dilator 202 at a tip end 204. Opposite the tip end 204 is a connection end 206 for connection to the patient suction tube 12. Dilator 202 defines a tip orifice having a diameter that is mechanically adjustable. Dilator 202 includes a series of plates 208 that are retracted to increase the diameter of the tip orifice upon rotation of a control ring 210. The plates 208 are connected to control ring 210 so that rotation of the control ring in one direction causes the plates 208 to rotate toward the center of tip end 204 thus reducing the diameter of the tip orifice. Rotation of the control ring 210 in the opposite direction causes the plates 208 to rotate away from the center of tip end 204 in manner similar to the plates in a conventional camera aperture. The plates 208 are arranged to provide a tip orifice that adjusts from less than ¼ of an inch to greater than ¾ of an inch.

During critical surgical situations requiring high suction flow rates, dilator 202 is opened to approximately a diameter of ¾ of an inch to increase the flow rate by utilizing the large diameter of the suction tip 200, patient tube 12, and pour spout 68. During delicate surgical situation in which the suction tip is required to keep the surgical field clear of small volumes of fluid, the dilator 202 is closed to a diameter of approximately ¼ of an inch. When dilator 202 is closed, the suction velocity through the tip orifice is increased permitting small drops of fluid to be removed. The dilator 202 permits the increased flow rate of the large diameter system to be constantly available while preserving the advantages of the flow characteristics of known small tip orifices.

The combined features of the invention 10, increasing the internal diameters of the patient vacuum tube 12 and the suction tip orifice over the range of ⅜ inch to 2 inches and the adaptive use of the pour spout 68 to maximize flow rate, positively effect patient mortality and morbidity. The advantages of conventional suction systems are preserved through the adjustable diameter tip orifice. However, it is to be understood that the present invention is not limited to the sole embodiment described above, but encompasses any and all embodiments within the scope of the following claims.

I claim:

1. A medical suction system tip comprising:

a nozzle defining a tapered lumen, said nozzle having a tip end dimensioned and configured for evacuating a substance from a patient and an attachment end, the tip end defining a tip orifice, the attachment end defining a discharge outlet having a larger internal cross sectional area than the tip end;

a handle having a first end for connection with a suction tube and second end, said handle defining a large lumen extending from the first end to the second end; and attachment means for releasably attaching said attachment end of said nozzle to said second end of said handle, whereby said attachment means permits the nozzle to be quickly removed during events requiring increased suction flow rate.

2. The suction system tip according to claim 1 wherein the lumen has a diameter between ⅜ of an inch and 2 inches inclusive at the attachment end of said nozzle.

3. The suction system tip according to claim 2 wherein the lumen has a diameter of approximately ¾ of an inch at the attachment end of said nozzle.

4. The suction system tip according to claim 2 wherein the inlet of said nozzle has a diameter of approximately ¼ of an inch.

5. A large diameter suction system comprising:

a suction tip having:

a nozzle defining a tapered lumen, said nozzle having a tip end dimensioned and configured for evacuating a substance from a patient and an attachment end, the tip end defining a tip orifice, the attachment end defining a discharge outlet having a larger internal cross sectional area than the tip end;

a handle having a first end for connection with a suction tube and second end, said handle defining a large lumen extending from the first end to the second end; and attachment means for releasably attaching said attachment end of said nozzle to said second end of said handle, whereby said attachment means permits the nozzle to be quickly removed during events requiring increased suction flow rate;

a suction canister having a spout port and a vacuum inlet port; and a suction tube connecting the discharge outlet with the spout port.

6. The suction system according to claim 5 wherein the discharge outlet, said suction tube, and the spout port each have an inside diameter of between ⅜ of an inch and 2 inches inclusive.

7. The suction system according to claim 5 wherein the lumen has a diameter of approximately ¾ of an inch at the attachment end of said nozzle.

8. The suction system according to claim 7 wherein the inlet of said nozzle has a diameter of approximately ¼ of an inch.

9. The suction system according to claim 5 wherein the spout port has a diameter of at least ½ of an inch.

10. The suction system according to claim 9 wherein said suction canister further includes a patient tubing port having a diameter no greater than ¼ of an inch.

11. The suction system according to claim 5 further including a first adapter impermanently sealing said suction tube to the spout port of said suction canister, and a second adapter impermanently sealing said suction tube to the connection end of said barrel.

* * * * *